United States Patent [19]

Ries et al.

[11] 4,170,143
[45] Oct. 9, 1979

[54] RECOGNIZING ULTRASONIC RESPONSE SIGNALS DURING TESTING OF STRUCTURAL MATERIALS

[75] Inventors: Karl Ries; Dieter Kaiser, both of Mülheim; Mesa Quaye, Kaarst; Heinz-Jürgen Boms; Klaus-Uwe Jannsen, both of Ratingen, all of Fed. Rep. of Germany

[73] Assignee: Mannesmann Aktiengesellschaft, Dusseldorf, Fed. Rep. of Germany

[21] Appl. No.: 823,704

[22] Filed: Aug. 11, 1977

[30] Foreign Application Priority Data

Aug. 11, 1976 [DE] Fed. Rep. of Germany ....... 2636401

[51] Int. Cl.$^2$ ............................................. G01N 29/04
[52] U.S. Cl. ............................................ 73/609; 73/629
[58] Field of Search ................. 73/596, 609, 610, 611, 73/612, 613, 620, 627, 659

[56] References Cited

U.S. PATENT DOCUMENTS

| | | | |
|---|---|---|---|
| 3,482,434 | 12/1969 | Cowan et al. | 73/609 |
| 3,813,926 | 6/1974 | Stubbeman | 73/609 |

*Primary Examiner*—Jerry W. Myracle
*Attorney, Agent, or Firm*—Smyth, Pavitt, Siegemund, Jones & Martella

[57] ABSTRACT

Ultrasonic response signals resulting from interaction of a test pulse with the structural material are recognized by dynamically tracking the noise level and adding thereto a fixed level; a response signal to be recognized must exceed the resulting variable threshold level.

4 Claims, 2 Drawing Figures

RECOGNIZING ULTRASONIC RESPONSE SIGNALS DURING TESTING OF STRUCTURAL MATERIALS

BACKGROUND OF THE INVENTION

The present invention relates to a method of automatically recognizing of ultrasonic response signals resulting from interaction of ultrasonic test signals transmitted into structural material for purposes of nondestructive inspection and flaw detection. The invention will find particular utility in the pulse testing of welding seams, but is applicable to other types of tests as well.

Generally speaking, ultrasonic, nondestructive tests are carried out in that test signals, usually, pulses are transmitted into a test object and a receiving transducer "listens" to a response. An evaluating scheme must be prepared to particularly identify ultrasonic response signals resulting from the interaction of a transmitted ultrasonic pulse with the structural material to be inspected and to discriminate such responses from noise and to identify and classify, if possible, specific types of response signals on the basis of established, usually empirically acquired criteria. This is true regardless whether the test is conducted by an individual or whether the test results and signals are evaluated automatically. The currently used test methods are carried out on the basis of extensive rules and guide lines which have been worked out for many known specific tests and types of tests. Standards have been established and adopted in a variety of ways; additional standards are being worked out.

One of the test parameters of importance is the so-called sensitivity as a criterium to distinguish noise from particular (but possibly rather low level) responses. The magnitude of the test sensitivity in any particular case is that quantity which determines the minimum signal amplitude to be recognized as information. This quantity by itself is not decisive as to the absolute flow detection capability or resolution of the particular test method and system as a whole.

The test sensitivity of test equipment is, for example, adjusted and determined by means of reference objects or by means of the so-called amplitude comparing method (see "Archiv' für das Eisenhüttenwesen", 11/1959, pgs. 693-703). Automatic test equipment meets the test sensitivity as per prescribed rules in that all signal peaks exceeding a set threshold level and occurring within a particular period of time (in which response signals or a particular response signal, if occurring at all, will, in fact, occur) will be recorded and/or inspected and analyzed further. Signal peaks below that level are regarded as noise to be rejected, the reason being that very small defects may produce, for example, very weak echos equal in amplitude to noise so that a reasonable distinction is no longer possible.

The absolute test sensitivity is further limited, for example, by unique properties of the test object, by the general conditions under which the test is conducted, and by the specific mode of coupling the test transducers to the test object. Furthermore, the noise of the electronic equipment driving and receiving the test transducers are factors which may effect the degree of discrimination between noise and information.

Noise is generally detected as a jittery oscillatory variation of the signal level as received with peaks extending up to a not too well defined amplitude level. This level must remain below the response threshold to which the system is adjusted, otherwise noise will be detected as information. However, if the level spread is too large, valuable information may be lost and the test will fail to yield detection results on smaller defects.

The response and threshold level is usually fixed in the case of automatic or semiautomatic testing. The noise level to be expected has been empirically ascertained, e.g., through prior test runs involving, e.g., a test object known to be free from defects. One can reasonably expect that such a threshold level remains valid for a longer period of time of testing. The tests are then conducted and the signals are evaluated by detecting signal amplitudes which exceed that response threshold.

Nonautomatic testing may well operate under utilization of signals below the noise peak level and the discrimination is left to the operator. Automatic equipment cannot be expected to distinguish between noise and information signal peaks of like amplitude, so that the response threshold for distinguishing noise from information and ultrasonic response signals must be set correspondingly high. On the other hand, the effective sensibility of the system may vary during a test, or during sequential tests involving the same or adjacent zones of the test object. That is to say that under comparable conditions, which should produce similar responses, the responses are, in fact, not similar because of changes in the system which changed its sensitivity. Amplitudes of signals being comparable to the adjusted threshold may register in one instance but not in the other on account of such variations.

Various ideas have been advanced to keep the sensitivity of the equipment constant. For example, a special test signal is transmitted into and through the test object along a well defined path, e.g., straight through or as V beam. The received signal is used for purposes of adjusting the system's sensitivity on subsequent tests. However, this method depends to a considerable extent on the local geometry of the test object which, on the other hand, should not have any bearing on the sensitivity. Also, either of a pair of transducers which cooperate for this special test, may undergo variations in coupling to the test object. It should be noted here that variations in the coupling between transducer(s) and test object(s) are one of the primary sources of variations in the systems sensitivity. Even if all other conditions, including error sources, remain similar, it is impossible to decide which of the two heads produces these variations, and, therefore, the variations in the system's sensitivity. Consequently, one does not know which of the two heads and which of the respective circuits have to be adjusted for compensation of the variations in sensitivity.

Another known method proceeds as follows. Two transducers are mounted in a common head so that their conditions of coupling to the test object are the same and any variation will influence both of them. One of these heads directs a control pulse straight down and receives a rear wall echo to be used as a reference. The circuit for the other transducer is then adjusted accordingly. However, if that other transducer transmits into a different direction, the sensitivity so adjusted is not really representative. Variations in coupling may be compensated but other variations in sensitivity based, e.g., on normal texture changes, different grain orientations, etc., may be missed. This type of sensitivity control is not very reliable and can actually cause a deterioration in the performance of the test equipment. Utilization of separate pulses for purposes of the system's adjustment, has the added disadvantage of introducing delays.

It can thus be seen that there is a need for greater consistency in the sensitivity of an ultrasonic test system particularly as far as recognizing ultrasonic response signals and classifying them in a manner that permits consistent detection of flaws and defects is concerned.

DESCRIPTION OF THE INVENTION

It is an object of the present invention to provide a new and improved method for recognizing and identifying ultrasonic response signals resulting from interaction of a structural material with an ultrasonic test signal which has been launched into the material.

It is another object of the present invention to eliminate the problems outlined above and to avoid interference in the recognition of ultrasonic response signals, due to variations in the coupling of the test equipment to the test object, normal variations in texture etc.

In accordance with the preferred embodiment of the present invention, it is suggested to detect and to track the existing noise level and to establish a response and threshold level for the recognition and isolation of ultrasonic response signals (following the transmission of a test signal interacting with the test object) which tracks the noise level at a safe distance therefrom, sufficient to eliminate noise, but varying therewith, so that, e.g. changes in coupling conditions, changes in texture and changes in the local geometry, all reflecting in a change in noise and background level, are compensated and the variations in the noise-from-information discriminating level cause the test sensitivity to remain constant. In addition, the noise level is used to ascertain proper functioning of the equipment because absence of noise is indicative of equipment malfunctioning, loss in coupling to the test object, etc.

By tracking the noise level and adjusting the response to ultrasonic signals for purposes of identifying them, it is no longer necessary to control as such the sensitivity (e.g. gain) in the ultrasonic receiver circuit. The dynamic threshold and discriminating level permits a truer classification and differentiation of ultrasonic signals as well as a better distinction from signals which meet some but not all criteria for classifying them as ultrasonic signals.

The method in accordance with the invention does not require separate ultrasonic control signals and pulses which is instrumental in speeding up the test process; the true test pulses can be sequenced in a more rapid rate. Also, special test runs and operation intervention for purposes of readjusting the system's sensitivity can be eliminated. Additionally, cross-checking, i.e., through x-raying the test object is no longer necessary.

DESCRIPTION OF THE DRAWING

While the specification concludes with claims particularly pointing out and distinctly claiming the subject matter which is regarded as the invention, it is believed that the invention, the objects and features of the invention and further objects, features and advantages thereof will be better understood from the following description taken in connection with the accompanying drawings in which:

Proceeding now to the detailed description of the drawings, FIG. 1 illustrates a test object 3 which is comprised, for example, of two plates or strips joined along edges by means of a welding seam 2. Ultrasonic test equipment is used to detect flaws or defects such as internal cracks, inclusions or the like, in the seam. The test equipment includes a test head 1 which is, for example, comprised of a transducer issuing a pulse of ultrasonic radiation, and subsequently it waits for a response during a particular period (looking window) following the transmission.

A beam of radiation is indicated by lines 4 whereby the dash-dot line represents the center of the beam. A defect in seam 2 will produce an echo which returns along the transmission path to be received by the transducer during a narrow time interval around the delay between the transmission of the leading edge of the transmitted pulse and a round trip of an ultrasonic wave along that path 4. A particular test, therefor, consists of operating the transducer in the transmit mode to launch an ultrasonic signal or burst of waves, followed by a change in mode to permit the transducer to operate as a receiver. The responses, if any, i.e., an echo of a flaw must occur within a particular period at the end of which another test can be conducted.

The test head 1 is moved along the seam 2, at a fixed distance therefrom and, possibly, in steps and in the direction of the arrow. Each transmitted pulse probes and inspects a limited zone of the welding seam 2, and the seam is inspected stepwise over its entire length as the head is moved along.

Figure 2:
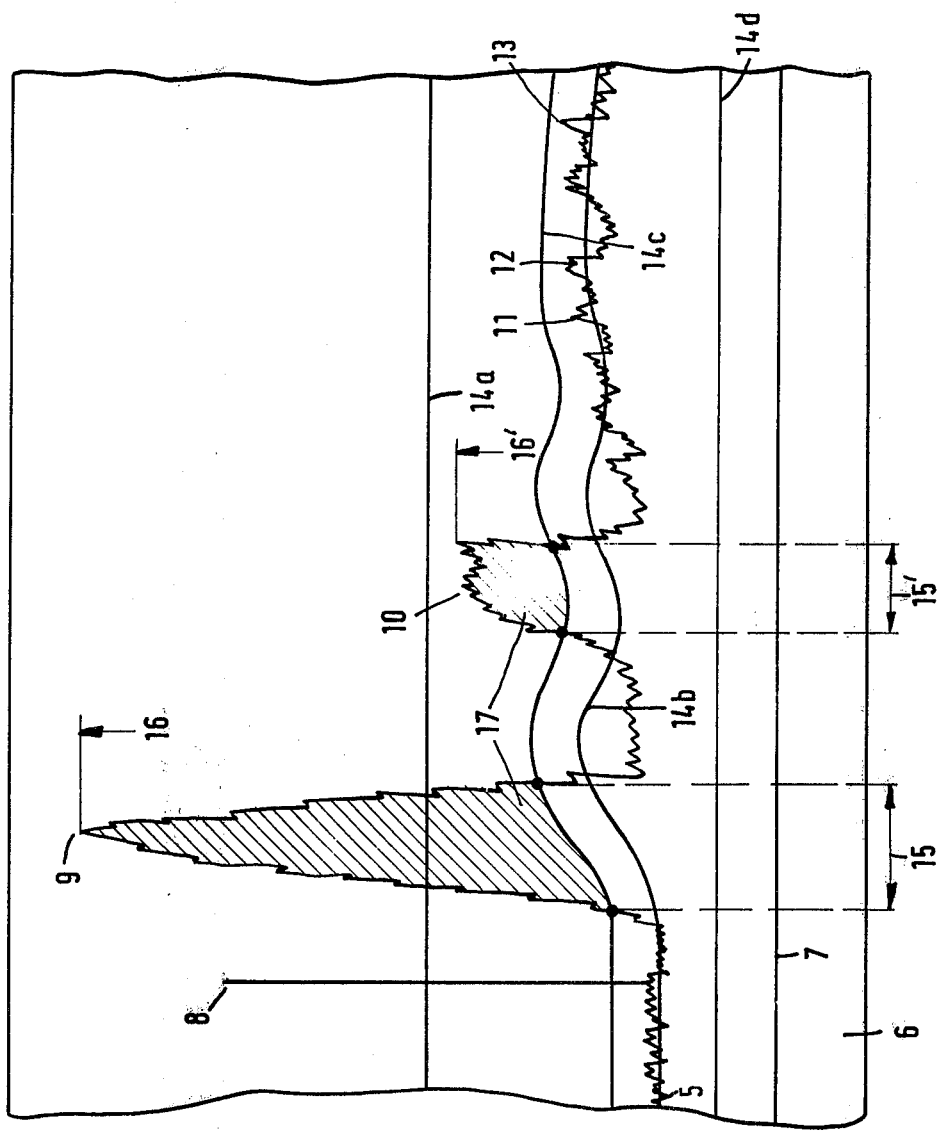
FIG. 2 is a graph of representative signal levels of the subsystem of FIG. 1 in conjunction with an example of response signals.

FIG. 2 illustrates a representative example of an ultrasonic signal 5 as received. The signal as such is the envelope of the ultrasonic vibrations as sensed by the transducer. The signal is presumed plotted on a chart 6 or the like for illustrative purposes. The signal portion illustrated may cover a period less than the entire period in which a response could occur. The looking period begins somewhat to the left of the Figure and the receiver waits for a response thereafter.

Reference numeral 7 refers to the zero level of the output being plotted. The signal 5 has a "normal" level above the zero line with a more or less irregular amplitude contour, but exhibiting rather little variations in the average signal level. The signal as plotted shows a variety of excursions. For example, peak 8 is a rather high, isolated noise peak, being very narrow and possibly of undefined origin. Peak 9 is the peak amplitude of a first response signal, e.g. of an echo of a transmitted pulse as received. 10 is also a flaw echo, but a much weaker one.

Excursions such as 11, 12 and 13 are local peaks above the "normal" noise level and resulting conceivably from secondary or tertiary interaction of the test beam with the structural material, possibly being parasitic modes or other noise generated due to the fact that there was a pronounced oscillatory stimulation of the material, and that all kinds of reflections should be expected having little to do with the task at hand.

Reference numeral 14a represents by way of example a fixed response level being located well above the noise level. The level 14a has been chosen so that all long term variations in detected noise levels on account of variations in the coupling of transducer 1 to the test object 3, and other causes, will not intrude into the circuit as information. Thus, if the circuit were adjusted to suppress all signals below level 14a, only noise peak 8 and the pronounced peak 9 would be recognized. The weak echo 10 would not be recognized as an ultrasonic response signal.

Figure 1:
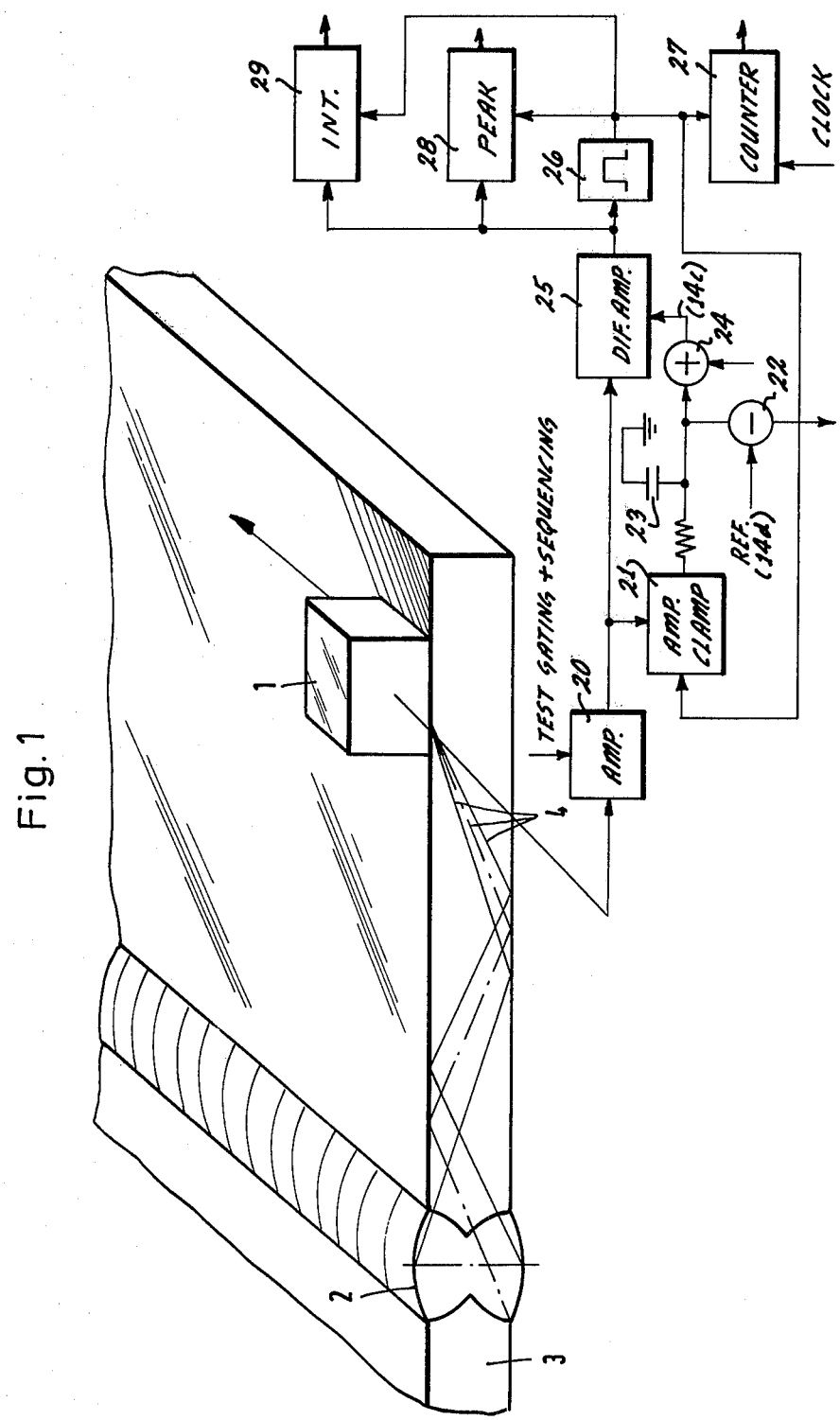
FIG. 1 is a schematic, perspective view with supplemental circuit block diagram of a test equipment and subsystem for practicing the invention.

The method in accordance with the invention requires the establishing of a different system response. As shown in FIG. 1, the output signal from the transducer in head 1 is fed to a gated preamplifier 20, which may be gated-on following the transmission of an ultrasonic signal and following settling and quiescing of the transducer in head 1 to serve as a receiving transducer. The output signal of amplifier 20 is fed to an isolating amplifier stage 21 as well as to a main amplifier 25 having an adjustable threshold. By way of example, amplifier 25 may be a differential amplifier for which the threshold level is established by a signal applied to the other one of the two inputs of that amplifier.

The output of amplifier 21 feeds an integrating or signal averaging stage 23. Amplifier 21 includes a clamping stage so that its output does not follow high peaks such as 9 and 10. In order to avoid excess settling time in the integrating circuit 23 following turn-on of the receiver circuit (gating of 20), the integrator may be constructed with a variable time constant, to begin with a short time constant so that the capacitor charges rapidly to the output level of the output level of amplifiers 20, 21. Subsequent increase of the time constant establishes true averaging conditions to eliminate the noise jitter for purposes of detecting the average noise level. Trace 14b in FIG. 2 depicts that noise level, being the signal at the output of averaging stage 23. It can be seen that this signal tracks the noise level, the time constant is comparatively long with reference to the noise frequency and the dominating portion of the noise spectrum.

A fixed bias is added to the noise tracking level by an algebraic summing stage 24, shifting the signal level from 14b to 14c. That bias is chosen to establish a level above the noise peak excursions. The invention is based on the observation that the noise level as such may vary but individual noise peaks are quite rare. In other words, the noise amplitude excusrions relative to the average level (14b) are considerably smaller than the level as such. Therefore, this bias for shifting the signal level up is not required to be too large in order to exclude the noise amplitude variations. Long term level changes in the noise as well as isolated excess peaks (8) are not eliminated by the averaging process per se.

The signal from summing stage 24 (signal level 14c) is used as a dynamic threshold level to control the threshold response of amplifier 25. Thus, amplifier 25 suppresses (preamlified) ultrasonic signals below the reference and dynamic threshold level 14c, are permits only larger signal excursions to pass. As to FIG. 2, only the hatched signal portions 17 are passed for further evaluation. The lower level peak 10 is well above the dynamic threshold 14c. Signals above that level are preliminarily classified as ultrasonic responses. It can be seen that the peak 8 can be sorted out on the basis of width: a signal must have also a certain duration before qualifying as an ultrasonic response signal.

The output of averaging stage 23 (signal level 14c) or the output of amplifier 21 are fed to a comparing stage 22 which compares this level with a reference signal (level 14d). This circuit monitors proper functioning of the system. As long as the system functions properly, a certain amount of noise is necessarily picked up by the transducer. If that noise level drops below the level 14d, it is likely that a malfunction has occurred, or that the transducer is no longer properly coupled to the test object. In other words, once the signal level as received drops below level 14d, it is no longer tracked, but a malfunction is signaled requiring, e.g., operator intervention.

The output signal of amplifier 25 is further processed to classify the signals permitted to pass. The output is squared and pulse-shaped by a stage 26 having two (logic) output levels, one (false) for output signals from amplifier 25 corresponding to a no-response situation because the ultrasonic signal remains below the dynamic response level 14b. The other output of 26 is a high signal whenever the ultrasonic signal exceeds level 14b.

The output of stage 26 is used as gating signal for a counter 27 which meters the duration of these excursions 9 and 10, i.e., it meters the periods such as 15 and 15' in FIG. 2. Whenever the output of stage 26 turns to false, the counter 27 may transfer its content and be reset to zero. The gating signal from 26 serves also as a control signal for a peak detector 28, detecting the amplitude peak levels, such as 16 and 16', and separately for each ultrasonic signal peak. An integrator 29 is also enabled by the gating signal from stage 26, to detect the area (hatching) for each ultrasonic signal excursion above the dynamic threshold 14c. All these values are then transferred further, stored, etc., for further use.

The gating signal from stage 26 could also be used as signal clamp for the isolating amplifier 21, clamping its output up to a fixed value so that the integration is not run up by the high signal excursion. However, a slight run up is desirable to set the dynamic threshold slightly higher for the recognition of the end of an ultrasonic response signal so that a definite end can be established rather than encountering an on-again, off-again condition on account of tail end noise of a true response.

The invention is not limited to the embodiments described above but all changes and modifications thereof not constituting departures from the spirit and scope of the invention are intended to be included.

We claim:
1. In a method of testing structural materials by ultrasonic inspection using individual test pulses, comprising the steps of:
    detecting a noise and background level in a signal path for received ultrasonic signals;
    detecting and recognizing ultrasonic response signals having resulted from interaction of the test pulses with the structural material by detecting signal levels above a threshold level; and
    varying the threshold level in accordance with the detected noise level to establish a dynamic response level for the ultrasonic signal detecting on the basis of tracking the noise level.
2. In a method as in claim 1, the first detecting step including the step of averaging the existing noise level, the varying step including the step of adding a fixed signal level to the averaged noise level to establish the dynamic response level.
3. In a method as in claim 1, and including the step of separately identifying response signals which exceed the threshold level.
4. In a method as in claim 1 and including the step of:
    detecting whether the noise level is above a minimum as an indication of operativeness of a system participating in the testing.

* * * * *